United States Patent
Fram et al.

(10) Patent No.: US 10,324,602 B2
(45) Date of Patent: *Jun. 18, 2019

(54) DISPLAY OF 3D IMAGES

(71) Applicant: MERGE HEALTHCARE SOLUTIONS INC., Hartland, WI (US)

(72) Inventors: Evan K. Fram, Paradise Valley, AZ (US); Murray A. Reicher, Rancho Santa Fe, CA (US); Howard T. Lam, San Diego, CA (US)

(73) Assignee: Merge Healthcare Solutions Inc., Hartland, WI (US)

( * ) Notice: Subject to any disclaimer, the term of this patent is extended or adjusted under 35 U.S.C. 154(b) by 210 days.

This patent is subject to a terminal disclaimer.

(21) Appl. No.: 15/076,390

(22) Filed: Mar. 21, 2016

(65) Prior Publication Data
US 2017/0038950 A1 Feb. 9, 2017

Related U.S. Application Data

(63) Continuation of application No. 13/872,920, filed on Apr. 29, 2013, now Pat. No. 9,324,188.
(Continued)

(51) Int. Cl.
*G06F 3/0354* (2013.01)
*G06F 3/0481* (2013.01)
(Continued)

(52) U.S. Cl.
CPC ...... *G06F 3/04845* (2013.01); *G06F 3/03543* (2013.01); *G06F 3/0412* (2013.01);
(Continued)

(58) Field of Classification Search
None
See application file for complete search history.

(56) References Cited

U.S. PATENT DOCUMENTS 5,511,157 A * 4/1996 Wang .................. G06F 3/04845
345/652
5,714,977 A * 2/1998 Mc Neil ............. G06F 3/04845
345/157
(Continued)

OTHER PUBLICATIONS

Restrict to XY Plane, downloaded @https://web.archive.org/web/20121224004646/http://www.3dmax-tutorials.com/idh_tb_constraints.html, available online since Dec. 24, 2012.*
(Continued)

*Primary Examiner* — Yingchun He
(74) *Attorney, Agent, or Firm* — Michael Best & Friedrich LLP

(57) ABSTRACT

The systems and methods of the present disclosure may provide, among other features, easy-to-learn, efficient, and/or unambiguous methods for controlling rotation and/or other manipulation of multi-dimensional (for example, 2D and/or 3D) images and/or objects. The systems and methods may be used for any type of image display/manipulation on a wide variety of computer systems and coupled displays including personal computers with monitors, phones, tablets, and televisions. In general, a user may select a particular rotation plane (for example, rotation only in x axis) by placement of a cursor, or touch of a finger, over a certain portion of the image such that subsequent movements of the mouse result in only rotations in the particular plane, and unwanted rotations and/or other manipulations in other planes do not occur. In this way, the user can more precisely control rotations of the 3D image and/or object.

20 Claims, 11 Drawing Sheets

Related U.S. Application Data

(60) Provisional application No. 61/640,553, filed on Apr. 30, 2012.

(51) Int. Cl.

| | | |
|---|---|---|
| *G06F 3/0484* | (2013.01) | |
| *G06T 19/20* | (2011.01) | |
| *G06T 3/60* | (2006.01) | |
| *G06T 19/00* | (2011.01) | |
| *G06F 3/041* | (2006.01) | |
| *G06F 19/00* | (2018.01) | |
| *G06F 3/0488* | (2013.01) | |

(52) U.S. Cl.
CPC ...... *G06F 3/04815* (2013.01); *G06F 3/04817* (2013.01); *G06F 3/04883* (2013.01); *G06F 19/321* (2013.01); *G06T 3/60* (2013.01); *G06T 19/00* (2013.01); *G06T 19/20* (2013.01); *G06F 2203/04802* (2013.01); *G06F 2203/04808* (2013.01)

(56) References Cited

U.S. PATENT DOCUMENTS

| | | | |
|---|---|---|---|
| 9,324,188 B1 | 4/2016 | Fram et al. | |
| 2004/0095318 A1 | 5/2004 | Morrison | |
| 2005/0024530 A1 | 2/2005 | Schuttinger | |
| 2007/0046625 A1 | 3/2007 | Yee | |
| 2008/0297471 A1 | 12/2008 | Hill | |
| 2009/0021475 A1* | 1/2009 | Steinle | G16H 40/63 345/156 |
| 2009/0060378 A1 | 3/2009 | Curtis | |
| 2010/0020025 A1 | 1/2010 | Lemort et al. | |
| 2010/0079493 A1 | 4/2010 | Tse | |
| 2011/0069019 A1 | 3/2011 | Carpendale | |
| 2011/0162066 A1* | 6/2011 | Kim | G06F 3/017 726/18 |
| 2011/0216090 A1 | 9/2011 | Woo | |
| 2011/0238535 A1 | 9/2011 | Stark | |
| 2012/0062489 A1 | 3/2012 | Andersson | |
| 2012/0254782 A1 | 10/2012 | Van Ieperen | |
| 2013/0215148 A1 | 8/2013 | Antonyuk | |
| 2014/0129990 A1 | 5/2014 | Xin et al. | |
| 2014/0229871 A1* | 8/2014 | Tai | G06F 3/04883 715/765 |

OTHER PUBLICATIONS

AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.

AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.

AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.

Aspyra's Imaging Solutions, 3 page color print out. Accessed at http://www.aspyra.com/imaging-solutions. Accessed on Feb. 9, 2015.

Avreo, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.

BRIT Systems, BRIT PACS View Viewer, 2 page color brochure, (BPB-BPV-0001). Downloaded from http://www.brit.com/pdfs/britpacsview.pdf. Accessed on Feb. 9, 2015.

BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.

BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.

CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.

Carestream, Cardiology PACS, 8 page color brochure. (CAT 866 6075 Jun. 2012). © Carestream Health, Inc., 2012. Downloaded from http://www.carestream.com/cardioPACS_brochure_M1-877.pdf. Accessed on Feb. 9, 2015.

Carestream, Vue PACS, 8 page color brochure. (CAT 300 1035 May 2014). © Carestream Health, Inc., 2014. Downloaded from http://www.carestream.com/csPACS_brochure_M1-876.pdf. Accessed on Feb. 9, 2015.

Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.

CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.

DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.

DR Systems, DR Scheduler User Guide, Release 8.2, 410 pages, (TCP-000115-A), © 19972009, DR Systems, Inc. Downloaded from https://resources.dominator.com/assets/003/6850.pdf. Document accessed Feb. 9, 2015.

FUJIFILM Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.

FUJIFILM Medical Systems, Synapse® Product Data, Synapse Release Version 3.2.1, Server Modules and Interfaces, 4 page color brochure, (XBUSSY085) Aug. 2008. Downloaded from http://www.fujifilm.com/shared/bin/server-interface.pdf. Accessed on Feb. 9, 2015.

FUJIFILM Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.

GE Healthcare, Centricity Pacs, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.

Handylife.com—Overview of Handy Patients Enterprise, in 2 page printout. Accessed from http://www.handylife.com/en/software/overview.html. Accessed on Feb. 18, 2015.

Handylife.com—Features of Handy Patients Enterprise, in 4 page printout. Accessed from http://www.handylife.com/en/software/features.html. Accessed on Feb. 18, 2015.

Handylife.com—Screenshots of Handy Patients Enterprise, in 2 page printout. Accessed from http://www.handylife.com/en/software/screenshots.html. Accessed on Feb. 18, 2015.

iCRco, I See The Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.

imageanalysis, dynamika, 2 page color brochure. Downloaded from http://www.imageanalysis.org.uk/what-we-do. Accessed on Feb. 9, 2015.

imageanalysis, MRI Software, in 5 page printout. Accessed at http://www.imageanalysis.org.uk/mri-software. Accessed on Feb. 9, 2015.

IMSI, Integrated Modular Systems, Inc., Hosted / Cloud PACS in one page printout. Accessed at http://www.imsimed.com/#!products-services/ctnu. Accessed on Feb. 9, 2015.

(56) References Cited

OTHER PUBLICATIONS

Infinitt, PACS, RIS, Mamma PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intererad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx.com/pacs.aspx. Accessed on Feb. 9, 2015.
McKesson Enterprise Medical Imagining and Pacs | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
Novarad Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacspius.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at http://www.healthcare.philips.com/main/products/healthcare_informatics/products/enterprise_imaging_informatics/1site_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/Intergy/. Accessed on Feb. 9, 2015.
Sclmage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at http://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra VISION, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
Viztek Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Touch Gesture Reference Guide. (Apr. 19, 2010). Retrieved Mar. 11, 2015 from http://lukew.com/ff/entry.asp?1071.
Shoemake, K. (Sep. 1992). ARCBALL: a user interface for specifying three-dimensional orientation using a mouse. In Graphics Interface (vol. 92, pp. 151-156).
Notice of Allowance from the U.S. Patent and Trademark Office for U.S. Appl. No. 13/872,920 dated Dec. 23, 2015 (17 pages).
Non-Final Office Action from the U.S. Patent and Trademark Office for U.S. Appl. No. 13/872,920 dated Mar. 20, 2015 (16 pages).
Final Office Action from the U.S. Patent and Trademark Office for U.S. Appl. No. 13/872,920 dated Sep. 22, 2015 (21 pages).
Applicant-Initiated Interview Summary from the U.S. Patent and Trademark Office for U.S. Appl. No. 13/872,920 dated 13/872,920 dated May 8, 2015 (3 pages).
Applicant-Initiated Interview Summary from the U.S. Patent and Trademark Office for U.S. Appl. No. 13/872,920 dated U.S. Appl. No. 13/872,920 dated Nov. 3, 2015 (3 pages).
Examiner-Initiated Interview Summary from the U.S. Patent and Trademark Office for U.S. Appl. No. 13/872,920 dated Dec. 23, 2015 (1 page).

\* cited by examiner

Start position for this example.

Starting gesture at the top or bottom restricts rotation to y-axis and only y-axis is shown Starting gesture at the side restricts rotation to x-axis and only x-axis is shown Starting away from the top, bottom and sides allows rotation along both axes, and both are displayed.

Start position for this example.

Moving 2 fingers together results in translation.

Moving 2 fingers apart increases magnification and moving together decreases magnification.

Rotating 2 fingers rotates along z-axis.

Starting gesture at the side restricts change to window level

Starting gesture at the top or bottom restricts change to window width only

Starting away from the top, bottom and sides allows change in both window width and level

DISPLAY OF 3D IMAGES

CROSS-REFERENCE TO RELATED APPLICATIONS

This application is a continuation of U.S. patent application Ser. No. 13/872,920, filed Apr. 29, 2013, with application claims the benefit of priority under 35 U.S.C. § 119(e) from U.S. Provisional Application No. 61/640,553, filed Apr. 30, 2012, titled "DISPLAY OF 3D IMAGES," the disclosures of each of which are hereby incorporated by reference in their entireties.

BACKGROUND

Many existing vendors offer software that creates and displays images, including the display of color or grayscale images that appear to be three dimensional. These images are typically based on data describing a volume of material or human tissue. In the field of medical imaging, devices such as CT, MRI, PET, and Ultrasound can generate data describing a volume of human or animal tissue. It is common for caregivers to display these volumes in a manner such that one or more images appear to be three dimensional using techniques such as volume rendering and surface shading. In addition, such software many enable the user to perform multi-planar reconstructions, maximum intensity pixel displays, or display grayscale or color slabs of various thickness and orientations.

When faced with a display of a three dimensional image, the user may want to rotate the image in any one of three axes or combinations thereof. Often, this rotation is controlled by an input device such as a mouse. For example, depression of a left mouse button combined with movement of the mouse from left to right might control rotation of the image from left to right (rotation about y axis), similar movement of the mouse away from or toward the user might control tilting of the image from toward or away from the perspective of the user (rotation about x axis) and some other sweeping movement of the mouse around the perimeter of the image in a near circular motion might control rotation of the image about the z axis. However, such mouse movements may be ambiguous, so that a user intending to rotate an image in the z axis may accidentally instead cause a rotation in the x axis (possibly in combination with movement in the z and/or y axes). Furthermore, a mouse may control other actions, such as cropping of the image in various planes, so that mouse movements intended to cause rotation may result in inadvertent cropping and other actions.

SUMMARY

The systems and methods of the present disclosure may provide, among other features, easy-to-learn, efficient, and/or unambiguous methods for controlling rotation and/or other manipulation of multi-dimensional, for example, 2D (two-dimensional) and/or 3D (three-dimensional), images and/or objects. The systems and methods may be used for any type of image display/manipulation on a wide variety of computer systems and coupled displays including personal computers with monitors, phones, tablets, and televisions. In general, a user may select a particular rotation plane (for example, rotation only in x axis) by placement of a cursor, or touch of a finger, over a certain portion of the image such that subsequent movements of the mouse (or other input device) result in only rotations in that particular plane, and unwanted rotations and/or other manipulations in other planes do not occur. In this way, the user can more precisely control rotations of the 3D image and/or object.

In an embodiment, a tangible computer readable medium is described that stores software instructions configured for execution by a computing system having one or more hardware processors in order to cause the computing system to perform operations comprising displaying a 3D medical object on a display of the computing system; receiving an first input from a user of the computing system at a particular location of the display, the first input comprising a touch input or a mouse click at the particular location and indicating initiation of a rotation function; accessing rotation rules associated with the 3D medical object, the rotation rules indicating planes of rotation available for rotating the 3D medical object based on the particular location of the first input; in response to determining that the particular location is to a side of the display, limiting rotation of the 3D medical object to rotations about a horizontal axis of the 3D medical object, such that the computing system does not allow rotation of the 3D medical object about any other axis until the rotation function is released; in response to determining that the particular location is to a top or bottom of the display, limiting rotation of the 3D medical object to rotations about a vertical axis of the 3D medical object, such that the computing system does not allow rotation of the 3D medical object about any other axis until the rotation function is released; in response to determining that the particular location is near the center of the display, limiting rotation of the 3D medical object to rotations about both the horizontal and vertical axes, such that the computing system does not allow rotation of the 3D medical object about any other axis until the rotation function is released; and receiving a second input from the user in order to initiate rotation of the 3D medical object about one or more of the horizontal and vertical axes.

According to an aspect, the tangible computer readable medium may further comprise, in response to determining that the particular location is to a side of the display, displaying one or more horizontal guide lines on the display, wherein the horizontal guide lines correspond to the horizontal axis; in response to determining that the particular location is to the top or bottom of the display, displaying one or more vertical guide lines on the display, wherein the vertical guide lines correspond to the vertical axis; and in response to determining that the particular location is near the center of the display, displaying one or more horizontal and vertical guide lines on the display, wherein the horizontal guide lines correspond to the horizontal axis and the vertical guide lines correspond to the vertical axis.

According to another aspect, the tangible computer readable medium may further comprise adjusting characteristics of the 3D medical object based at least in part on the rotation function.

In another embodiment, a computer-implemented method of manipulating a multi-dimensional object in an electronic environment is described comprising, as implemented by one or more computer systems comprising computer hardware and memory, the one or more computer systems configured with specific executable instructions, providing to a user, on an electronic display, a multi-dimensional object; receiving, from the user, a rotation selection input; determining a restriction on the manipulation of the multi-dimensional object based at least in part on the rotation selection input; receiving, from the user, an object manipulation input; and manipulating the multi-dimensional object based at least in part on both the object manipulation input and the restriction on the manipulation.

According to an aspect, the computer-implemented method may further comprise, in response to an input from the user, displaying, on the electronic display, one or more guide lines indicating one or more available rotation selection inputs, wherein the received rotation selection input is selected from the one or more available rotation selection inputs.

According to another aspect, the input from the user comprises at least one of: movement of a cursor or touching of the electronic display near the multi-dimensional object, movement of a cursor or touching of the electronic display on the multi-dimensional object, movement of a cursor or touching of the electronic display near one or more of the guide lines, movement of a cursor or touching of the electronic display on one or more of the guide lines, and movement of a cursor to or touching of a particular portion of the electronic display.

According to yet another aspect, displaying the one or more guide lines comprises determining boundaries of the multi-dimensional object; and displaying the one or more guide lines based on the determined boundaries of the multi-dimensional object, wherein the one or more guide lines do not overlap with the multi-dimensional object.

According to another aspect, the characteristics of the one or more guide lines are dynamically adjusted to allow the user to easily recognize the one or more guide lines, wherein the characteristics comprise at least one of a position, a spacing, and a thickness.

According to yet another aspect, the guide lines are removed from the electronic display in response to receiving the object manipulation input from the user.

According to another aspect, the rotation selection input comprises at least one of: placing a cursor or touching the electronic display at a particular portion of the multi-dimensional object, placing a cursor or touching the electronic display at one or more of the guide lines, placing a cursor or touching the electronic display at an arced icon, pressing a button on a mouse while placing a cursor in proximity to one or more of the guide lines, touching a particular portion of the electronic display.

According to yet another aspect, the restriction on the manipulation of the multi-dimensional object comprises at least one of: allowing rotation of the multi-dimensional object on only one particular axis, and allowing rotation of the multi-dimensional object on only two particular axes.

According to another aspect, receiving an object manipulation input comprises the user sliding a finger from one location on the electronic display to another location on the electronic display.

According to yet another aspect, the multi-dimensional object comprises a 3D object, wherein manipulating the 3D object comprises, in response to the user touching the electronic display on a side of the display and sliding the finger vertically, rotating the 3D object on an x axis; in response to the user touching the electronic display on a top or bottom of the display and sliding the finger horizontally, rotating the 3D object on a y axis; and in response to the user touching the electronic display near a middle and sliding the finger in any direction, rotating the 3D object on at least one of both the x axis and the y axis, and a z axis, wherein the rotation of the 3D object is proportional to a distance the finder is slid.

According to another aspect, receiving an object manipulation input comprises the user moving an electronic indicator from one location on the electronic display to another location on the electronic display.

According to yet another aspect, the multi-dimensional object comprises a 3D object, wherein manipulating the 3D object comprises, in response to the user making a selection with the electronic indicator on a side of the display and moving the electronic indicator vertically, rotating the 3D object on an x axis; in response to the user making a selection with the electronic indicator on a top or bottom of the display and moving the electronic indicator horizontally, rotating the 3D object on a y axis; in response to the user making a selection with the electronic indicator near a middle and moving the electronic indicator in any direction, rotating the 3D object on at least one of both the x axis and the y axis, and a z axis; and in response to the user selecting an icon with the electronic indicator and moving the electronic indicator in any direction, rotating the 3D object on at least one of both the x axis and the y axis, and a z axis, wherein the rotation of the 3D object is proportional to a distance the electronic indicator is moved.

According to another aspect, the electronic indicator comprises at least one of a mouse pointer and a cursor.

According to yet another aspect, receiving an object manipulation input comprises the user touching the electronic display at two or more locations, and manipulating the multi-dimensional object comprises, in response to the user touching the electronic display in two places, and sliding the two places in a substantially same direction, translating the multi-dimensional object; in response to the user touching the electronic display in two places, and sliding the two places in substantially opposite directions, changing the size of the multi-dimensional object; and in response to the user touching the electronic display in two places, and rotating the two places, rotating the multi-dimensional object.

According to another aspect, manipulating the multi-dimensional object includes at least one of adjusting characteristics of the multi-dimensional object and adjusting viewing properties of the multi-dimensional object, wherein viewing properties include at least one of a window level and a window width.

According to yet another aspect, manipulating the multi-dimensional object includes rotating the multi-dimensional object along particular axes, wherein the particular axes are defined based on correlation with characteristics of the multi-dimensional object.

In yet another embodiment, a computer system is described comprising one or more hardware processors in communication with a computer readable medium storing software modules including instructions that are executable by the one or more hardware processors, the software modules including at least: a user interface module configured to display a multi-dimensional object on an electronic display; a user input module configured to receive a first input from a user at a particular location of the electronic display, the first input comprising a mouse click or touch input at the particular location and indicating initiation of a rotation function; an object rotation module configured to access rotation rules associated with the multi-dimensional object, the rotation rules indicating planes of rotation available for rotating the multi-dimensional object based on the particular location of the first input, the object rotation module further configured to: in response to determining that the particular location is near a vertical guide line, limiting rotation of the multi-dimensional object to rotations about a horizontal axis of the multi-dimensional object, such that the object rotation module does not allow rotation of the multi-dimensional object about any other axis until the rotation function is released; in response to determining that the particular location is near a horizontal guide line, limiting rotation of the multi-dimensional object to rotations about a vertical axis of the multi-dimensional object, such that the object rotation module does not allow rotation of the multi-dimensional object about any other axis until the rotation function is released; in response to determining that the particular location is near a particular icon, limiting rotation of the multi-dimensional object to rotations about an axis perpendicular to a surface of the electronic display, such that the object rotation module does not allow rotation of the multi-dimensional object about any other axis until the rotation function is released; and receiving via the user input module a second input from the user in order to initiate rotation of the multi-dimensional object about one or more of the horizontal, vertical, and perpendicular axes.

BRIEF DESCRIPTION OF THE DRAWINGS

The following aspects of the disclosure will become more readily appreciated as the same become better understood by reference to the following detailed description, when taken in conjunction with the accompanying drawings.

DETAILED DESCRIPTION

The systems and methods of the present disclosure may provide, among other features, easy-to-learn, efficient, and/or unambiguous methods for controlling rotation and/or other manipulation of multi-dimensional (for example, 2D and/or 3D) images and/or objects. Although the description and examples discussed herein relate to medical images, the systems and methods could be used for any type of image display/manipulation on a wide variety of computer systems and coupled displays including personal computers with monitors, phones, tablets, and televisions. Particular input mechanisms are discussed herein with reference to various example embodiments. However, other input mechanisms are usable. For example, any examples discussed with reference to touch screen inputs may also be implemented using inputs from a mouse, voice commands, gestures, and/or any other type of input. Similarly, any examples discussed with reference to mouse-based inputs may also be implemented using touch inputs from a touch-sensitive device, voice commands, gestures, and/or any other type of input.

In one embodiment, the computing system 150 (discussed in detail below with reference to FIG. 1), or any other computing system, displays 2D and/or 3D images and allows a user to rotate and/or manipulate the 2D and/or 3D images using controls that are discussed below. In general, a user may select a particular rotation plane (for example, rotation only in x axis) by placement of a cursor (also referred to as an electronic indicator) over a certain portion of the image such that subsequent movements of the mouse (or other input device) result in only rotations in that particular plane, and unwanted rotations and/or other manipulations in other planes do not occur. In this way, the user can more precisely control rotations of the 3D image and/or object. As used herein, a "plane of rotation," and "rotation plane" each describe an image plane that is perpendicular to the axis about which rotations are performed. Thus for rotation about the x axis, the rotation plane is the plane defined by the y and z axes.

Example Image Rotation

Figure 2:
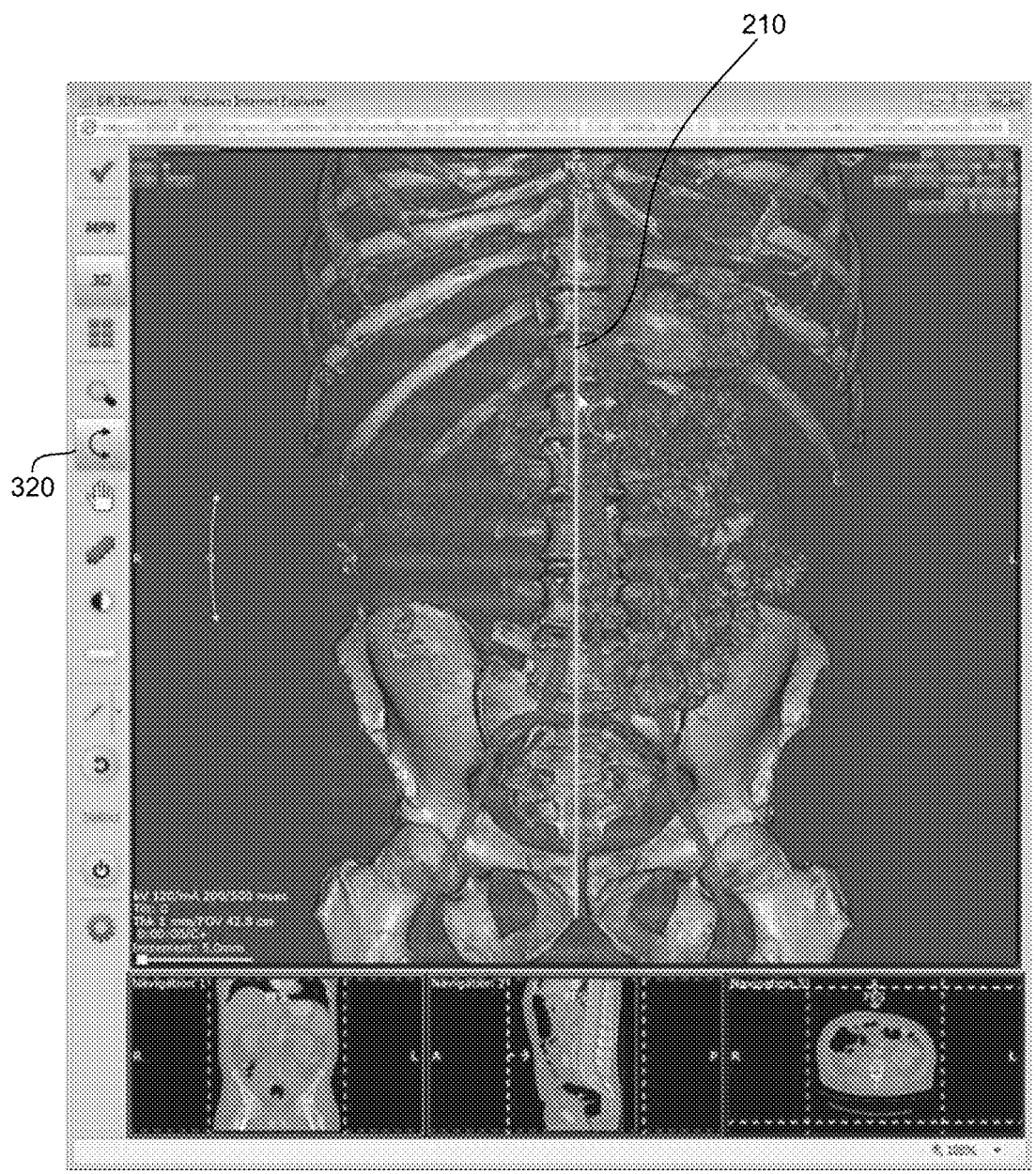
FIGS. 2-4 illustrate sample user interfaces that may be displayed by the system in which 3D images may be viewed and controlled, according to embodiments of the present disclosure.

FIG. 2 illustrates a sample user interface that may be displayed on a display of the computing system 150 (for example a computer monitor or a tablet). In this example, the user interface depicts a 3D medical image. In the example of FIG. 2, in response to the user positioning the cursor (or electronic indicator) roughly over the midline of the image (for example, midline relative to left and right), the computing system displays a yellow vertical guide line 210 on that midline to indicate that from the current mouse position, the mouse can be moved up and down along the line in order to tilt the image forward or backward about the x axis. In one embodiment, no matter what other tool might otherwise be in use, moving the mouse to the midline of the image causes the vertical yellow guide line 210 to appear and the displayed tool to change to the rotate tool 320. This functionality may provide one or more benefits, such as removing the need for the user to manually change tools to access the rotation function and/or allowing the user to unambiguously tilt the image on the x axis (or other axes, as discussed below). In other embodiments, the guide line 210 may have different display characteristics, such as different length, color, position, etc. In addition, in some embodiments, the guide line 210 may be replaced with a different indicator of a currently selected rotation plane, such as an icon or text that is placed on the screen near the cursor or at a fixed location.

Figure 3:
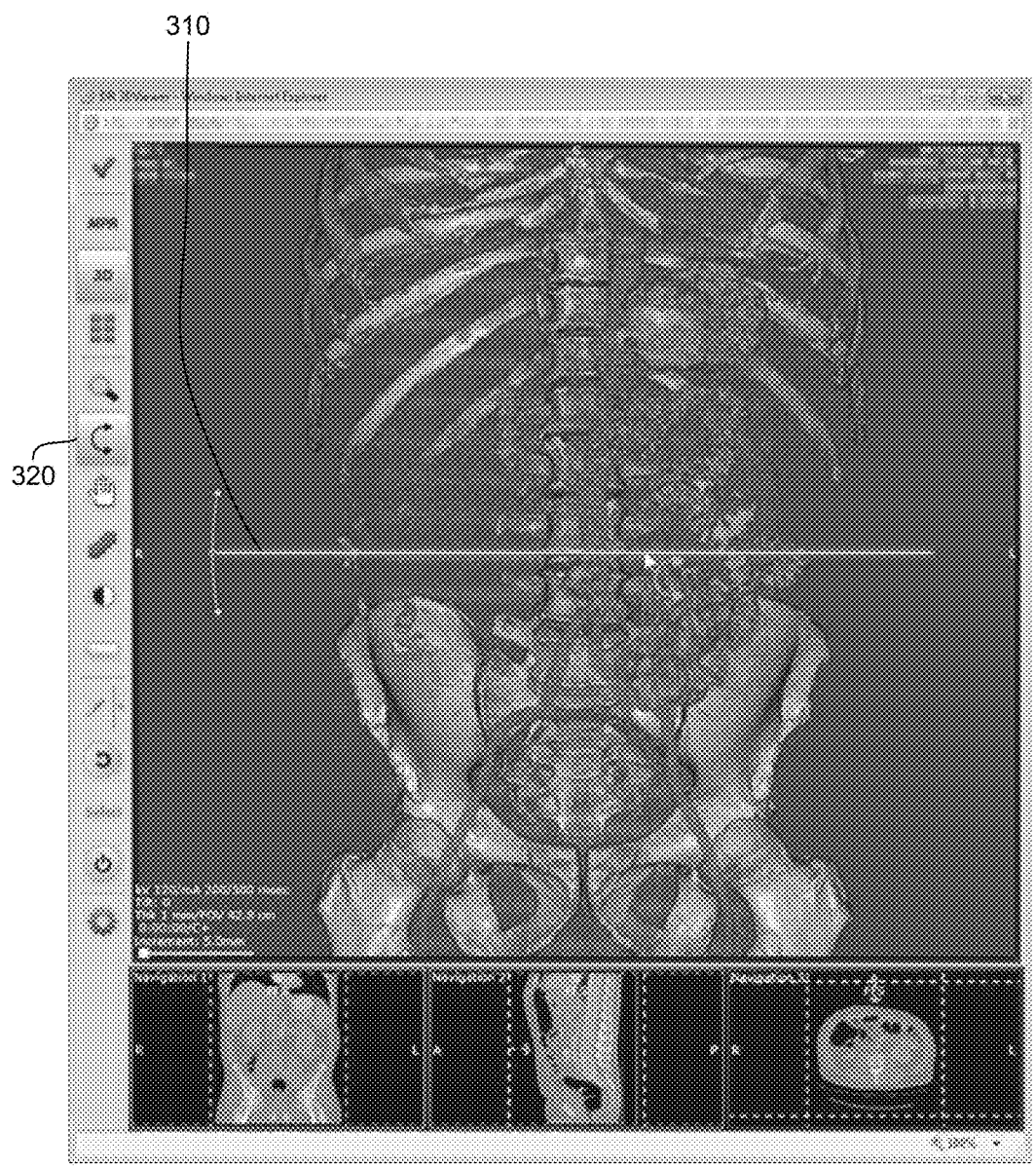

FIG. 3 illustrates the same user interface as FIG. 2, but now with rotation about the y axis selected. In this embodiment, the user has limited and/or restricted the rotation function to rotations about the y axis by moving the mouse near the midline of the image relative to the superior/inferior aspect (for example, top and bottom) of the image in order to cause a horizontal yellow guide line 310 to appear. In this embodiment, when the guide line 310 appears, the tool icon also changes to the rotate icon 320 indicating that movements of the mouse will cause the 3D image to rotate about the y axis so that the user can rotate the image from left to right (or vice versa) by moving the mouse along the guide line 310, without accidentally rotating the image about the y or z axis in the process.

Figure 4:
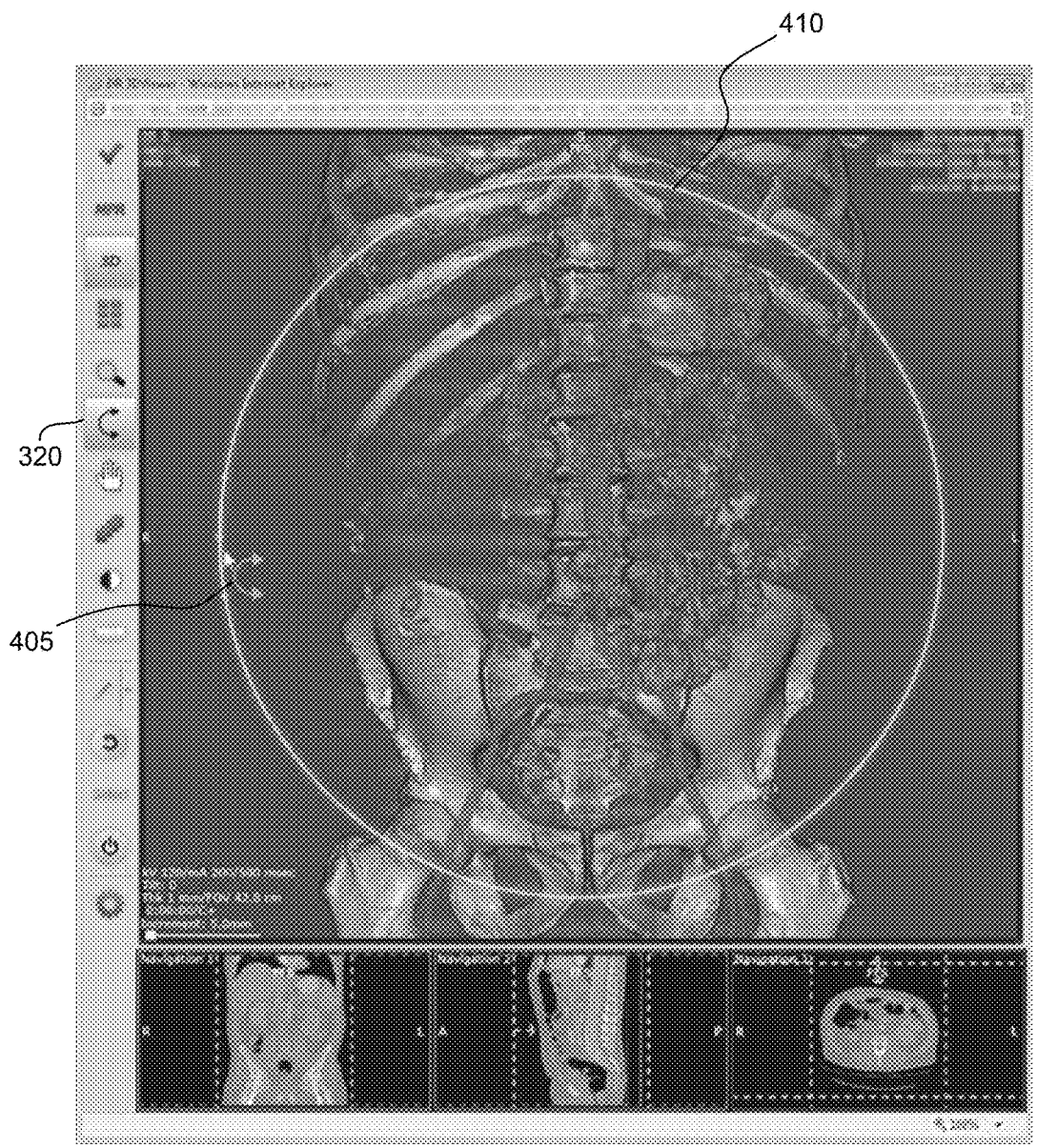

FIG. 4 illustrates the same user interface as FIGS. 2 and 3, but now with rotation about the z axis selected. In this embodiment, the user has limited and/or restricted the rotation function to rotations about the z axis by moving the mouse over the arced icon 405 that is positioned to the left of the image in this example. In response to positioning of the pointer over the arced icon 405, the rotate icon 320 is selected and a guide circle 410 appears. The user can then rotate the image about the z axis by moving the cursor along the guide circle 410.

As noted above, any other visual cues (for example, other than the illustrated guide lines 210, 310 and guide circle 410) may be used in other embodiments. Additionally, other forms of cues may be provided, such as audible or tactile feedback, to indicate a selected rotation axis.

In one embodiment, rotating the image does not require the user to precisely move the mouse along the path of the various vertical, horizontal, or circular guides. For example, in one embodiment, with rotation around the y axis selected (for example, FIG. 3), mouse movements with any vector in the left or right direction will cause the image to rotate in only the horizontal rotation plane so long as the left mouse button is depressed. Any other input, such as a key or key combination, may similarly maintain selection of a rotation axis despite movement of the cursor outside of the guide line or circle. For the user, the experience simulates grabbing the yellow guide line and then sliding along it. In the embodiment noted above, when the left mouse button is released, if the user drags the mouse away from the displayed guide line, the system returns to whatever tool or function was in use prior to the rotation.

User preferences or system preferences may be set to determine when the guide lines appear relative to the position of the cursor. For example, moving the mouse to within 2, 5, or 7 pixels, or some percentage of an image pixel height or width, of midline might cause the guide line to appear. In addition, there may be user preferences controlling the appearance of the guide lines (color, thickness, style, shape, arrows, etc.) or other icons that appear in relation to this invention.

In one embodiment, if the mouse is moved to the intersection point or points that would activate the pop-up of two lines or a line plus circle, the user may control two axes of rotation at once.

Therefore, the systems and methods discussed herein provide a simple, intuitive and unambiguous method for rotating images along three axes while retaining quick access to any other tool(s) or function(s) previously in use.

Example Device Implementations

Figure 5A:
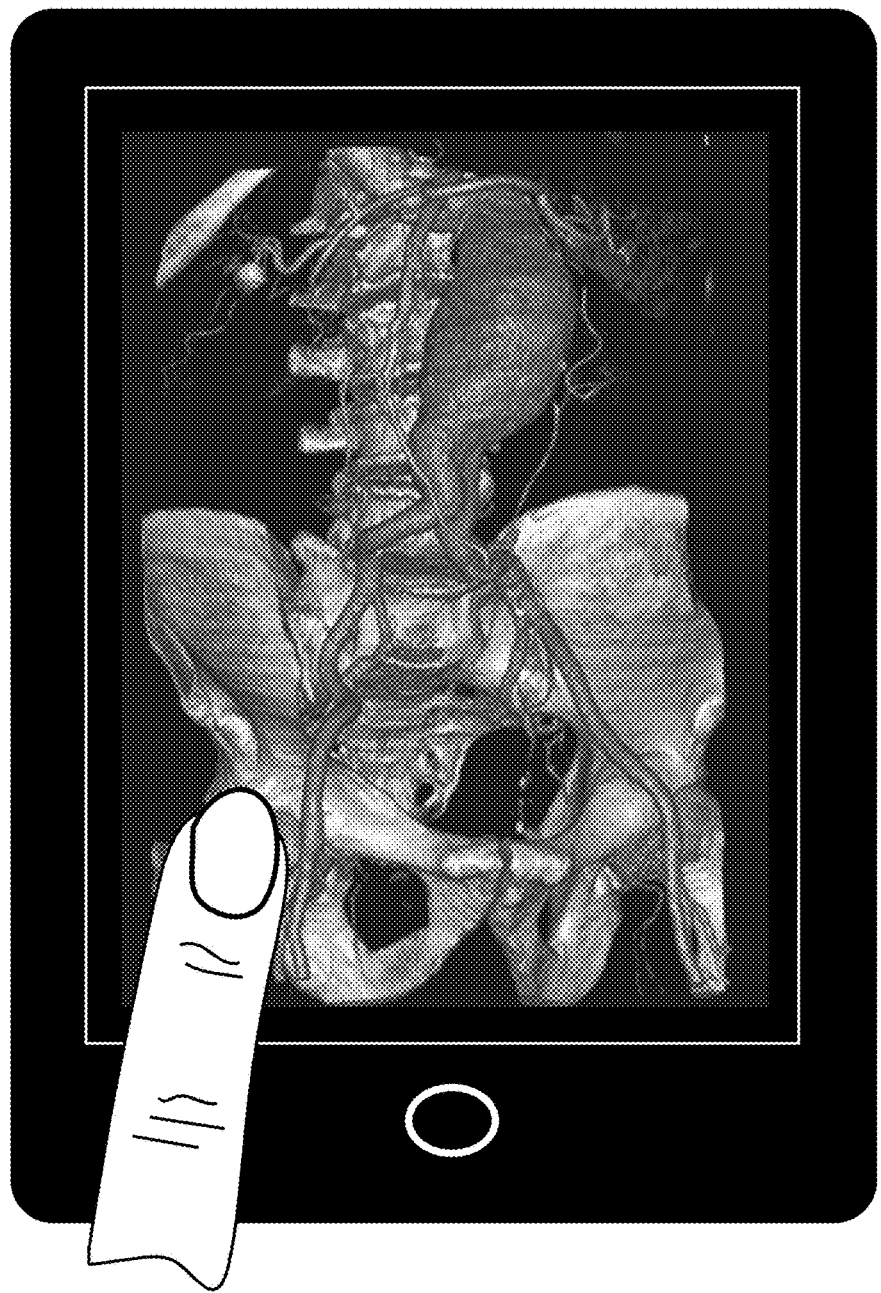
FIG. 5A illustrates a sample user interface of a mobile device in which 3D images may be viewed and controlled through touch input from a user, according to an embodiment of the present disclosure.
Figure 5B:
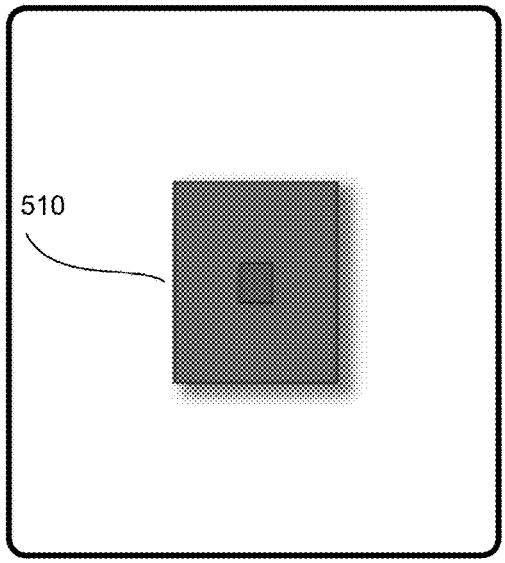
FIGS. 5B-5E illustrate sample user interfaces of the system in which 3D images may be viewed and controlled through touch input from a user, according to an embodiment of the present disclosure.

FIGS. 5A-5E illustrate example user interfaces that are displayed on a mobile or other computing device. The computing device may include any available device, such as a cell phone, smart phone, tablet computer, laptop, desktop or any other computing device 150. In one embodiment, the computing device has an input device that is touch sensitive, such that commands may be provided to rotate the displayed image via the user touching the display or other touch sensitive input device with one or more fingers. However, in other embodiments the user interface may be controlled by other input devices, such as a mouse, keyboard, or voice commands, for example. In the example of FIG. 5A, a 3D medical image is illustrated on a mobile device, such as a mobile phone or tablet that is touch sensitive and able to detect multiple fingers touching the display. In the examples of FIGS. 5B-5E, a 3D object 510, a rectangular prism, is illustrated for ease of illustration and discussion in this disclosure. However, any other image or object, such as medical images, schematic images, or any other image, may be used in place of the object 510.

Figure 5D:
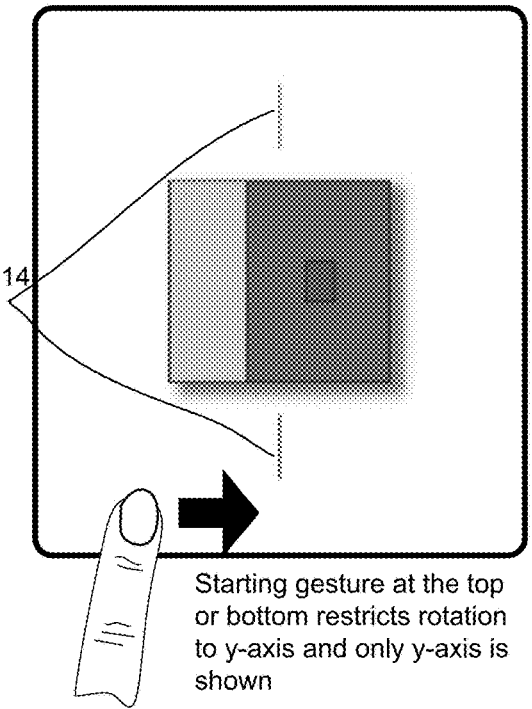
Figure 5C:
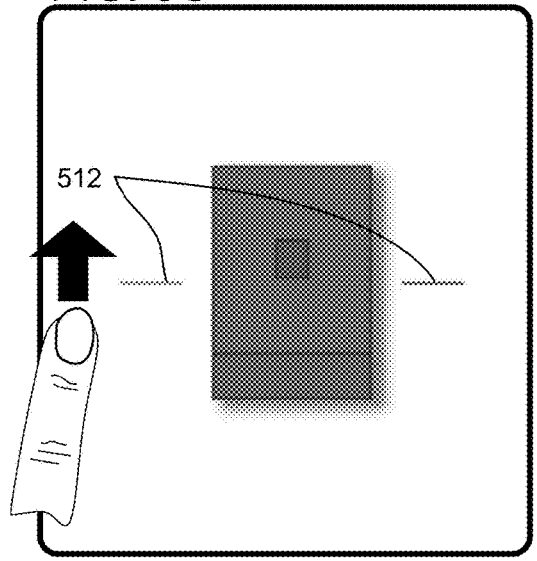
Figure 5E:
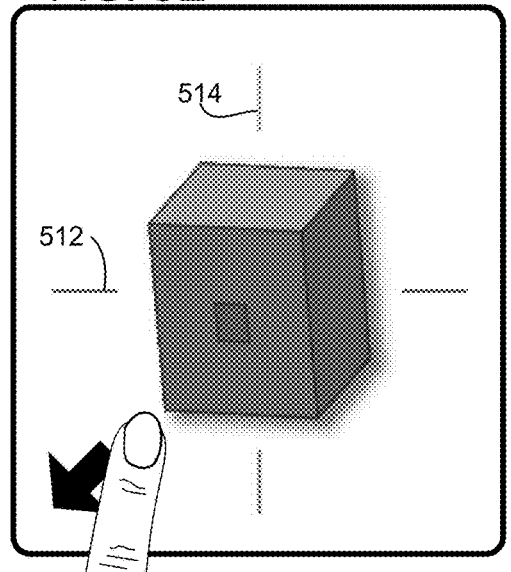

In the embodiment illustrated in FIGS. 5A-5E, the user can control which axes are available for rotation of the 3D object based on a screen position from which rotation is initiated. In this embodiment, the x axis is horizontal and the y axis is vertical. For example, if rotation is initiated with a finger touch, or cursor movement, in the left or right margins of the user interface, such as in FIG. 5C, the rotation of the image is only possible about the x axis. For example, in response to the user initiating contact with the touch sensitive input device along the side of the screen, horizontal guide lines 512, as illustrated in FIG. 5C, indicate that rotation is only available around the x axis. Similarly, if rotation is initiated with a finger touch, or cursor movement, to an upper or lower margin of the user interface, such as is shown in FIG. 5D, the rotation of the image is only possible around the y axis. This is shown in FIG. 5D by display of the vertical guide lines 514, which indicate that rotation is only available around the y axis. In the examples of FIGS. 5C-5E, the horizontal guide lines 512 are positioned at the x axis and the vertical guide lines 514 are positioned at the y axis.

In one embodiment, the user can control which axes are available for rotation of the 3D object based on a screen position from which rotation is initiated. In this embodiment, the screen position may be related to (or referenced from) a display frame displayed on the screen rather than the entire screen itself. For example, a screen might contain two or more display frames which display 3D images. By touching within a display frame the user may both indicate the active display frame and select the axis of rotation, as above, by first touching a position along the top, bottom, or side of the display frame.

In one embodiment, rather than choosing the restricted axis of rotation by first touching the top, bottom, or side of a display frame or screen, the user may choose the restricted axis of rotation by touching adjacent to an object. For example, touching the screen to the left or right of the object may indicate that rotation is to be restricted to the x axis, and touching above or below an object may indicate that rotation is to be restricted to the y axis.

While the systems and methods discussed herein refer to rotations about and x axis, y axis, and/or the z axis, in other embodiments rotations may be about other axes. For example, in one embodiment a user can select an axis of rotation that does not directly aligned with an X, Y, or Z axis of the image or object. Similarly, in some embodiments the software may be configured to define axes that correlate with and/or are otherwise related to characteristics of an object to be rotated. For example, in one embodiment the available axes of rotation may vary based on the type of 3D volume containing the object or objects being viewed, such as an MRI, CT, or ultrasound scanners. In another embodiment, the axes of rotation may be related to a structure within the 3D volume. For example, a radiologist viewing a 3D display of a patient's spine from a volumetric CT scan may prefer that rotations are performed about a long axis of the spine for the purpose of efficiently interpreting the exam. Due to asymmetric patient positioning or anatomical asymmetry within the patient, the patent's spine may be obliquely oriented with regard to the acquired imaging volume. Thus, in an embodiment, the imaging volume may be rotated so that the x, y, and z axes are aligned relative to the patient's anatomy, such as to allow the patient's spine be aligned along the y axis. In other embodiments, the imaging volume may not be rotated, but a new rotational axis (e.g., not the x, y, or z axis) may be determined (either manually by the user or automatically by the computing system) in order to allow rotations about a different axis (such as the long axis of the patient's spine). In addition, in some embodiments, the x, y, and/or z axes may relate to a collection of objects, a single object, a single object within a collection of objects, and/or a camera angle.

In this embodiment, the image can be rotated in both the x and y axes by initiating rotation with a finger touch, or cursor movement (or other predefined input), within a central region of the user interface, such as is illustrated in FIG. 5E. As shown in FIG. 5E, rotation is available around both the horizontal and vertical axes, as indicated by display of both the horizontal guide lines 512 and the vertical guide lines 514 indicating rotation about the x axis and y axis respectively. In some embodiments, the user may select rotation around only a z axis by initiating rotation at a particular location, such as the center of the image. In those embodiments, an indicator such as the guide circle discussed above with reference to FIG. 4 may be displayed to indicate to the user that rotation is limited and/or restricted to rotations around the z axis. Rotation around the z axis may be performed in other manners, such as the multi-touch methods discussed below.

In other embodiments, selection of the axis-specific rotation functions may be performed in different manners. For example, a first gesture may be performed on a touch sensitive display in order to select rotation around only the x axis (for example, FIG. 5C), while a second gesture may be performed in order to select rotation around only the y axis (for example, FIG. 5D). In another embodiment, a voice commands may be provided to select rotation around one or more axes. Any other commands or inputs may be used to select axis specific rotation functionality.

Figure 6A:
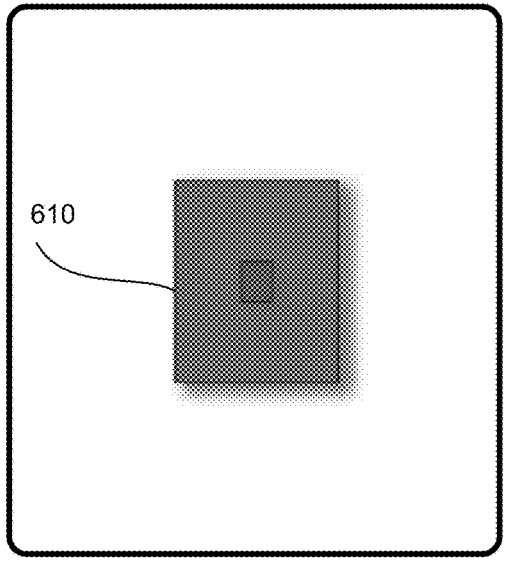
FIGS. 6A-6D illustrate sample user interfaces of the system in which 3D images may be viewed and controlled through multiple touch input from a user, according to an embodiment of the present disclosure.
Figure 6C:
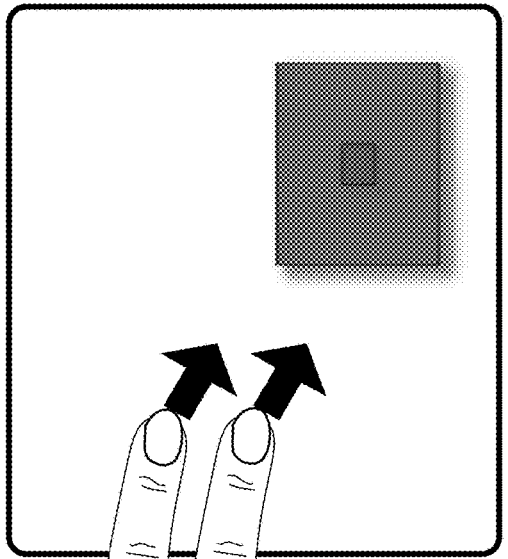
Figure 6B:
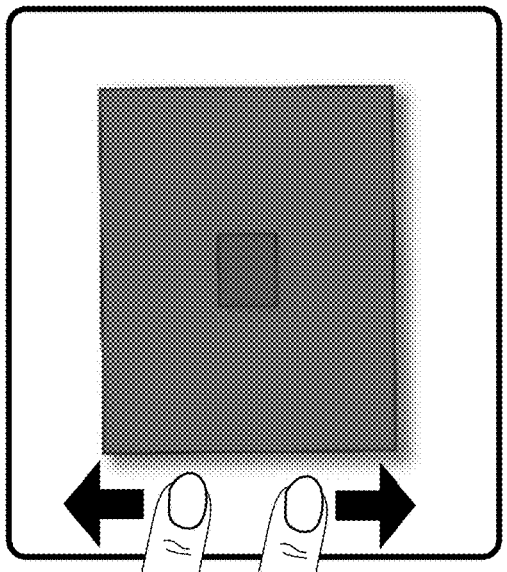

FIGS. 6A-6C illustrate additional controls that are available on a touchscreen device with multi-touch. In one embodiment, the controls illustrated in the embodiments of FIGS. 6A-6C may be used in conjunction with the rotation functionality discussed with reference to FIGS. 5A-5D. FIG. 6A illustrates a start position of an image 610, which may be any 3D object or any 2D image.

In the embodiment of FIG. 6B, a resize operation is being performed by the user adjusting the distance between two fingers that are touching the screen. For example, as the user moves the fingers apart, the 3D object appears to increase in size and, likewise, as a user moves the fingers together, the 3D object appears to decrease in size. Thus, the user can easily resize the image using multi-touch functionality.

FIG. 6C illustrates the user moving the three-dimensional object by movement of two fingers in the same direction. For example, if both fingers are substantially uniformly moved down on the screen, the three-dimensional image is moved down. Similarly, if both fingers are substantially uniformly moved left or right, the three-dimensional image is shifted left or right, respectively. Accordingly, the user can easily adjust a position of the three-dimensional image. For larger images, such image translation commands may be used to move from one section of an image to another.

Figure 6D:
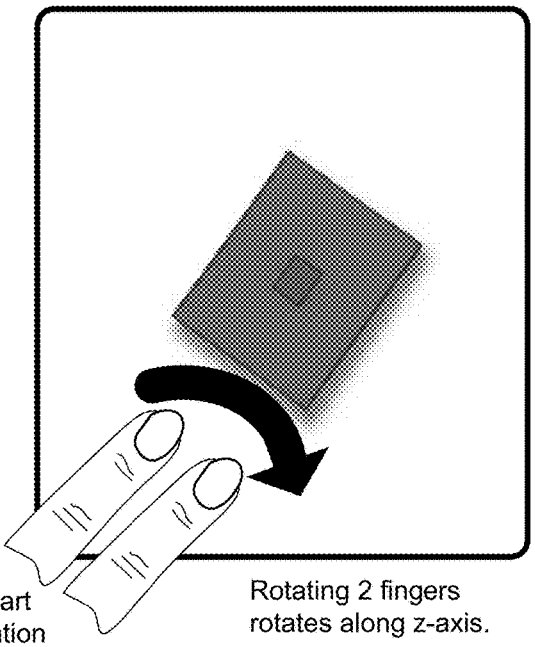

In the example of FIG. 6D, the user is able to rotate the 3D object around the z axis (for example, spinning the image clockwise or counterclockwise) by adjusting the orientation of the two fingers that are each touching the display. For example, in the illustration of FIG. 6D, the two finger are rotating clockwise and the image is correspondingly rotated clockwise. Thus, the user can easily rotate the 3D object about the z axis, possibly in conjunction with the rotation features discussed above with reference to FIG. 5. While manipulation of a 3D object is discussed with regard to the operations illustrated in FIG. 6A-6D, the user interface described could be used to manipulate 2D images.

In some embodiments, all three operations described in reference to FIGS. 6B, 6C, and 6D may occur simultaneously. In other embodiments, the multitouch or mouse movement discussed herein could control different axes than the ones described in the examples.

Example Image Adjustments

Figure 7A:
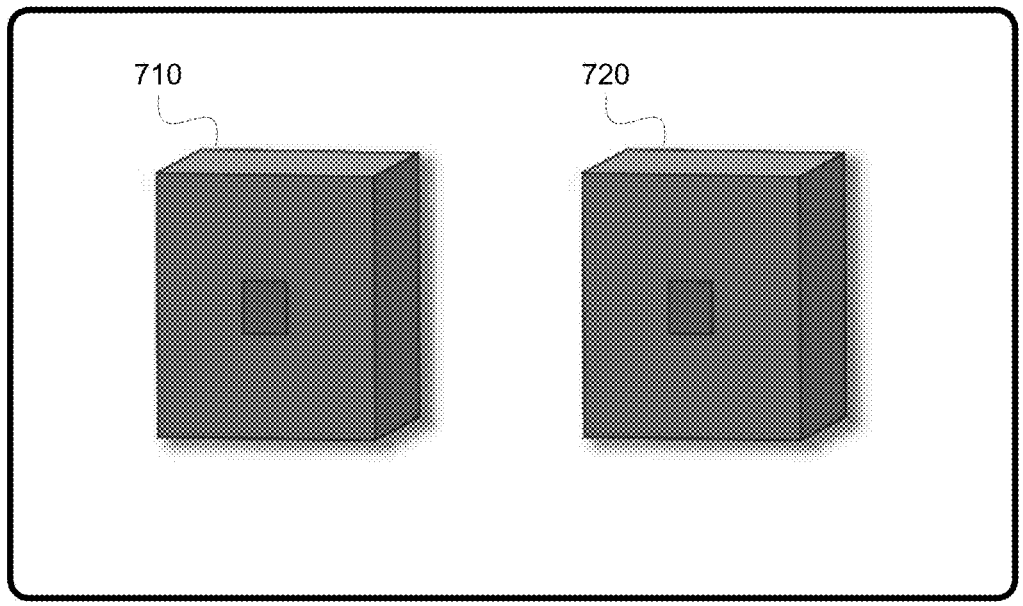
FIGS. 7A-7B illustrate sample user interfaces of an example 3D CAD system wherein properties of the displayed 3D objects may be controlled through touch input from a user, according to an embodiment of the present disclosure.
Figure 7B:
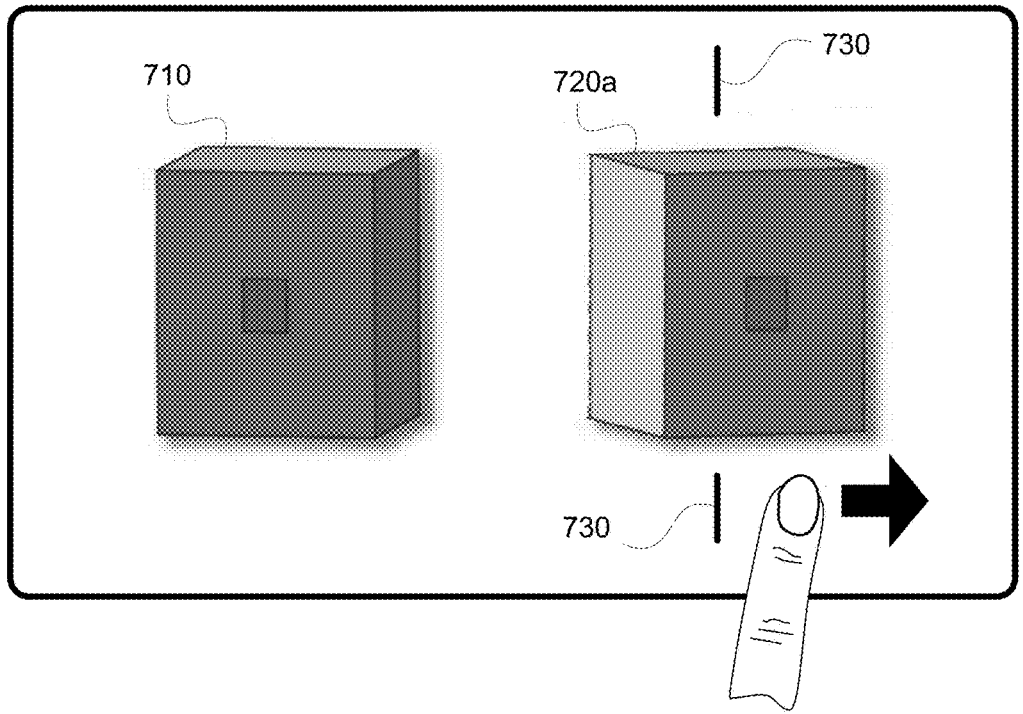

In some embodiments, rather than adjusting the view of an object, such as discussed above (for example, changing a view rotation, magnification, translation, etc.), the user interface systems and methods discussed herein may also be used to adjust actual properties of objects in 3D space. For example, objects that are drawn in a computer aided drafting (CAD) application (or any other image generation/modification application) may be resized or rotated using the methods discussed above such that the actual properties of the objects in 3D space are modified. FIG. 7A illustrates an example 3D CAD project with two 3D objects 710 and 720 that each have the same orientation. FIG. 7A may represent a display screen of a mobile or desktop computer device. In this embodiment, the user can select individual objects and adjust properties of the objects with reference to the 3D space (and the remainder of the CAD project). For example, in FIG. 7B the user has rotated the object 720 about its y axis so that it now has an orientation that is different than the orientation of the object 720 in FIG. 7A, and different than the orientation of the other object 710 in FIGS. 7A and 7B. The rotation of the object 720 may be performed in a similar manner as discussed above with reference to changing views of objects, for example, rotations about the y axis may be selected by initiating rotation with a touch below or above the object 720. Similarly, if the user initiates the rotation operation by first touching his finger over the object he can rotate about both x and y axes and if the user first touches to a side of the object, rotation is restricted to rotation about the x axis. In the embodiment of FIG. 7B, the locked rotation axis is shown with guide lines 730 to indicate that rotation is locked to rotations about the y axis.

In one embodiment, the methods discussed could be used to simultaneously select both the object to manipulate, and the rotation axis to lock. For example, touching the screen near an object may both select the object for manipulation and lock the rotation axis based on the touch position relative to the nearest object.

In one embodiment, touching the edges of the display frame may be used to select a mode in which the view of the entire collection of objects may be changed. In this embodiment, the position at which the screen is touched may be used to select how the scene should be rotated, using, for example, the method described with reference to FIG. 5. For example, touching the top or bottom of the display frame may restrict rotation of the scene around the y axis, while first touching a side of the screen may restrict rotation about the x axis.

Figure 8A:
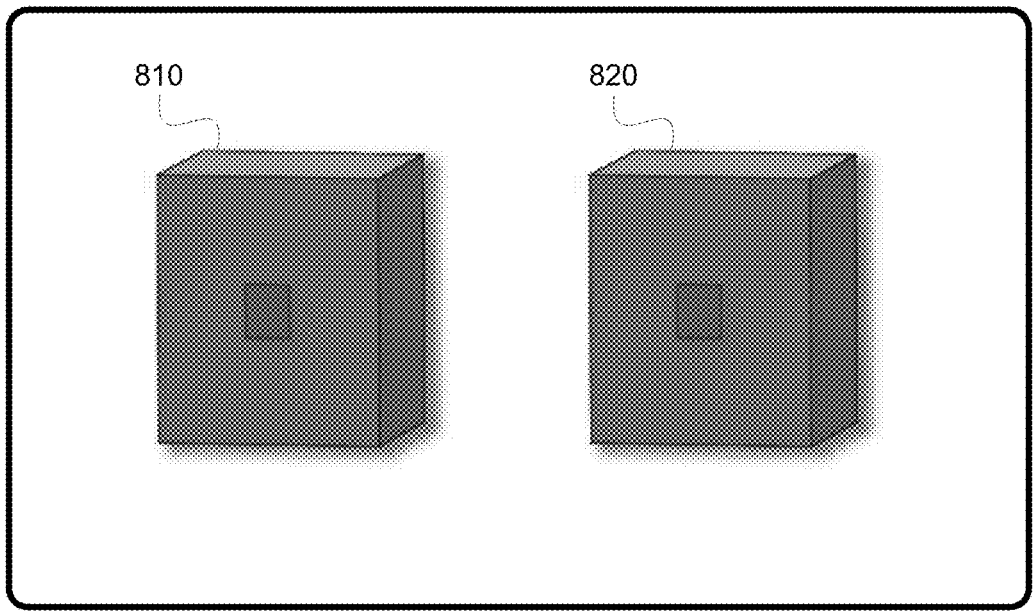
FIGS. 8A-8B illustrate sample user interfaces of an example 3D CAD system wherein properties of the displayed 3D objects may be controlled through multiple touch input from a user, according to an embodiment of the present disclosure.
Figure 8B:
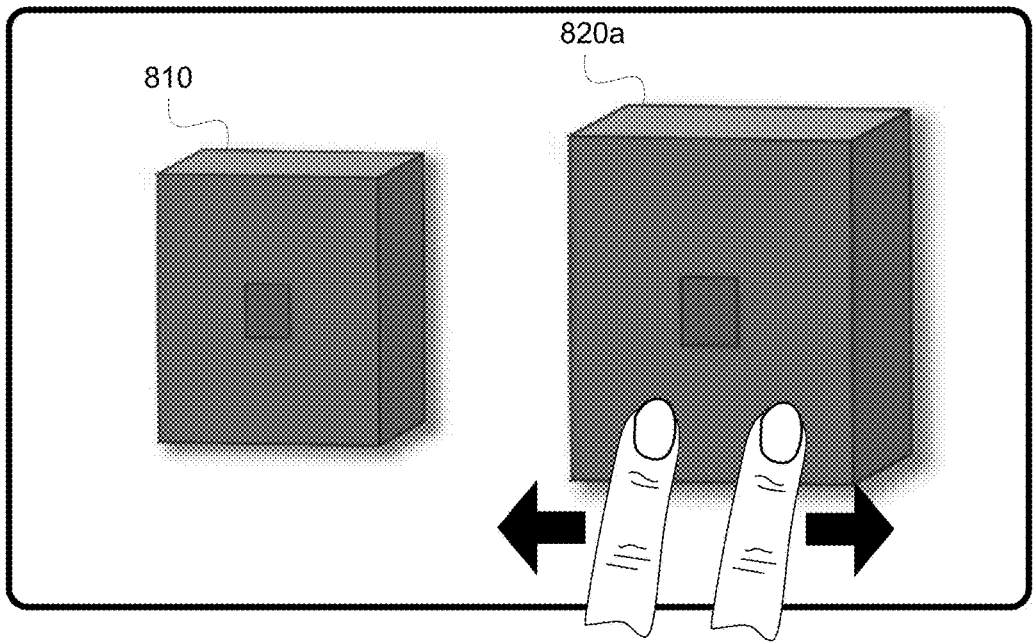

FIGS. 8A and 8B are another example of a CAD application. Using two finger multitouch operations like those illustrated in FIGS. 6B, 6C, and 6D, the user can translate an object, rotate it about the z axis, or change the size of an object. The object that is the subject of the operation may be selected by the user first touching the screen on or near the object. In the example of FIG. 8B, the user started the operation by touching the screen over an object, selecting it for magnification.

Adjustments of Other Display/Image Characteristics

Figure 9A:
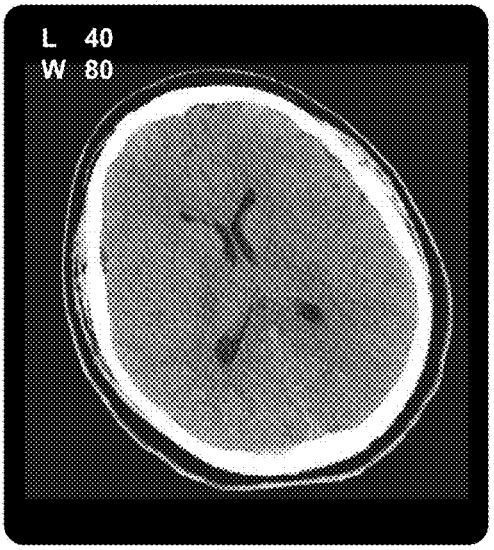
FIGS. 9A-9D illustrate sample user interfaces of the system in which 2D images may be viewed and the properties of 2D objects may be controlled through touch input from a user, according to an embodiment of the present disclosure.

In addition to adjusting the rotation, position, zoom level, etc. of objects in the manner discussed above, in some embodiments the user interface functionality discussed above can be used to adjust other properties of images or objects, including viewing properties (for example, how stored objects are displayed without necessarily changing the actual stored object) and/or object properties (for example, actually changing characteristics of an image or 3D object). In general, the systems and methods discussed herein may be used to select and/or modify properties of images or objects that can be changed in response to characteristics of an initial touch (or other predefined command, such as a mouse click, voice command, gesture, etc.) with a user interface, while keeping other properties locked. For example, FIGS. 9A-9D illustrate other example characteristics of images that can be adjusted in one embodiment. FIG. 9A illustrates a sample medical image, an image from a brain CT scan, which is displayed with a window width of 80 and a window level of 40. FIG. 9A serves as the initial state in this example, serving as the baseline for each of the actions described with reference to FIGS. 9B, 9C, and 9D.

Figure 9B:
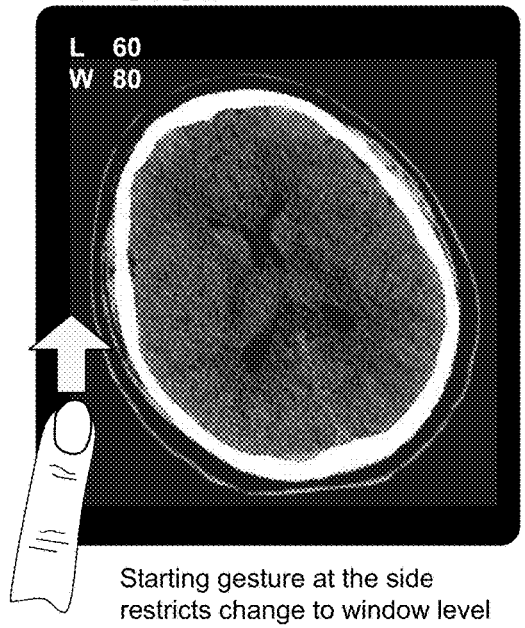

In this example, touching the display at a side of the object (e.g., the head anatomy depicted in the medical image of FIGS. 9A-9D) or side of a display, such as is illustrated in FIG. 9B, causes movements of the user's finger up and down on the display to adjust only the window level (and/or brightness in some embodiments) of the medical image. Thus, with the window level adjustment selected (for example by initially touching to the left of the image) the user can move up and down on the image in order to adjust the window level without worrying about changing other characteristics of the image. Only the component of finger motion up and down is processed to adjust window level, with components of motion in the left and right direction ignored by the system (or possibly associated with another process in some embodiments).

Figure 9C:
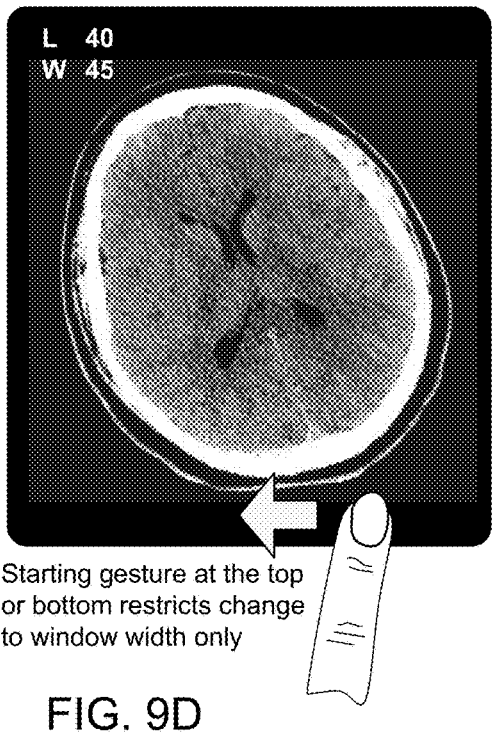

In FIG. 9C, the user has selected adjustment of window width (and/or contrast in some embodiments) by initially touching the display below the medical image, preventing adjustment of window level. In other embodiments, the same type of selection could be made by initially touching above the medical image, at the top of the display region, or at the bottom of the display region. Accordingly, with the window width adjustment selected, the user can move left and right on the image in order to adjust the width without worrying about adjusting other characteristics of the image. Only the component of finger motion left and right is processed to adjust window width, with components of motion in the up and down direction ignored by the system (or possibly associated with another process in some embodiments).

Figure 9D:
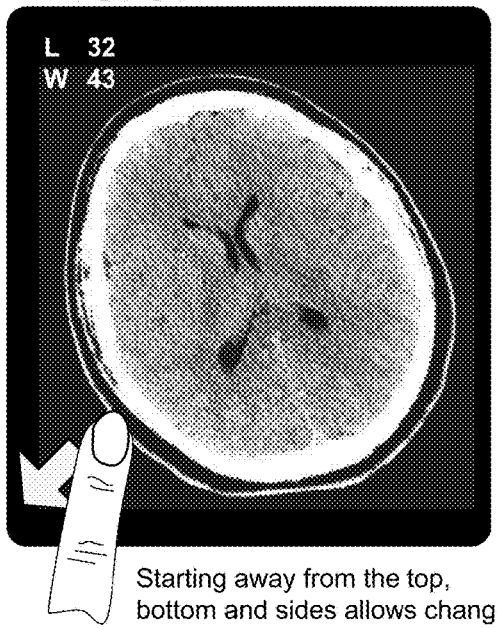

Finally, in FIG. 9D the user has enabled adjustments of both the window width and level by initially touching the display away from the top, bottom, and sides, and subsequently moving their finger in any direction. Components of finger motion left and right, and up and down, are processed to adjust window width and level, respectively.

Additional Features

As noted above, the systems and methods described herein may provide, among other features, easy-to-learn, efficient, and/or unambiguous methods for controlling rotation and/or other manipulation of 2D and/or 3D images and/or objects. In addition, various embodiments of the systems and methods provided herein provide one or more of the following advantages:

1. Restricted Object Rotation

In some embodiments, when rotation is allowed only about a single axis (for example, rotation is restricted to be about a single axis) using any of the methods discussed above, movement of a cursor (or finger in a touchscreen embodiment) in only a single direction causes rotation and/or other manipulation about that selected axis. For example, with reference to FIG. 5D, rotation about the y axis is selected and movement of the user's finger left or right on the screen causes the image to rotate about the y axis. However, any component of movement of the user's finger up or down on the screen does not cause rotation of the image around the y axis, or any other axis. Thus, with the rotation locked about the y axis only movements in the perpendicular direction (for example, left and right on the screen) cause rotation about the y axis. Likewise, if rotation about the x axis is selected, such as in FIG. 5C, only movements up and down on the screen causes rotations about the x axis, and movements from left to right do not cause rotations about the x axis, or any other axis.

2. Guide Line Display with Cursor Proximity to Object

In some embodiments, guide lines appear in response to positioning and/or movement of a cursor (or finger in a touchscreen embodiment) over or near (for example, within a predetermined number of pixels of) an object to be rotated or other portion of a display, such as the x and y axes (whether visually displayed or not) or border of a user interface. This is in contrast to embodiments having the guide lines constantly displayed once a 3D rotation tool is selected. As discussed above, the various guide lines may appear as the user moves a cursor (or a finger touch on a display screen) to different areas surrounding an image to be rotated. Additionally, guide lines that show only the currently available axis (or axes) of rotation may be displayed to avoid confusion regarding the currently selected rotation axis.

3. Guide Line Display with Cursor Proximity to Image Axis

In some embodiments, guide lines appear as a user approaches an image axis (for example, the x or y axis of an image). For example when the cursor (or finger touch) approaches the x axis (for example, is within five, or some other number of, pixels of the x axis), a guide line may appear. In one embodiment, such rotation guide lines may appear and be available for rotation of an image when the user has another image manipulation tool selected (for example, the system does not require a 3D rotation tool to be selected in order to cause the guide lines to appear and rotations to be implemented).

In one embodiment, with a guide line displayed, the user activates a 3D rotation mode by providing another action, such as a left mouse click. With the 3D rotation mode selected, the user can initiate 3D rotations with movements, such as those discussed above. In one embodiment, once the user activates the 3D rotation mode, the selected guide line(s) disappears (or changes one or more display characteristics). In such embodiments, the 3D rotation mode may still be active (for example, until the user releases the left mouse button), but the guide line does not obfuscate the image. In other embodiments, the selected guide line disappears (or changes one or more display characteristics) in response to the cursor moving away from the guide line (for example, moving more than five pixels away from the x axis).

4. Guide Line Display Non-Overlapping with Object

In some embodiments, guide lines that indicate the currently available axis (or axes) of rotation are displayed outside of the actual image to be rotated. For example, with reference to FIG. 5D, the guide lines 514 do not overlay the displayed 3D object, but instead are shown outside of the object. Accordingly, the guide lines 514 clearly indicate that rotation about the y axis is available without obscuring the image. Likewise, with reference to FIG. 5E, guide lines 512 and 514 are shown to indicate that rotation about the x axis and the y axis is available, still without obscuring any of the displayed object. Depending on the embodiment, the position, spacing, thickness, and/or other characteristics of guide lines may be dynamically adjusted by software to allow the user to best recognize the guide lines. For example, in one embodiment the system determines boundaries of an object to be rotated and then presents guide lines on either side of the object, such that a smaller object would have guide lines that are closer together and a larger object would have guide lines that are further apart, such that the guide lines do not obscure the objects but are close to the objects.

Example Operation

Figure 10:
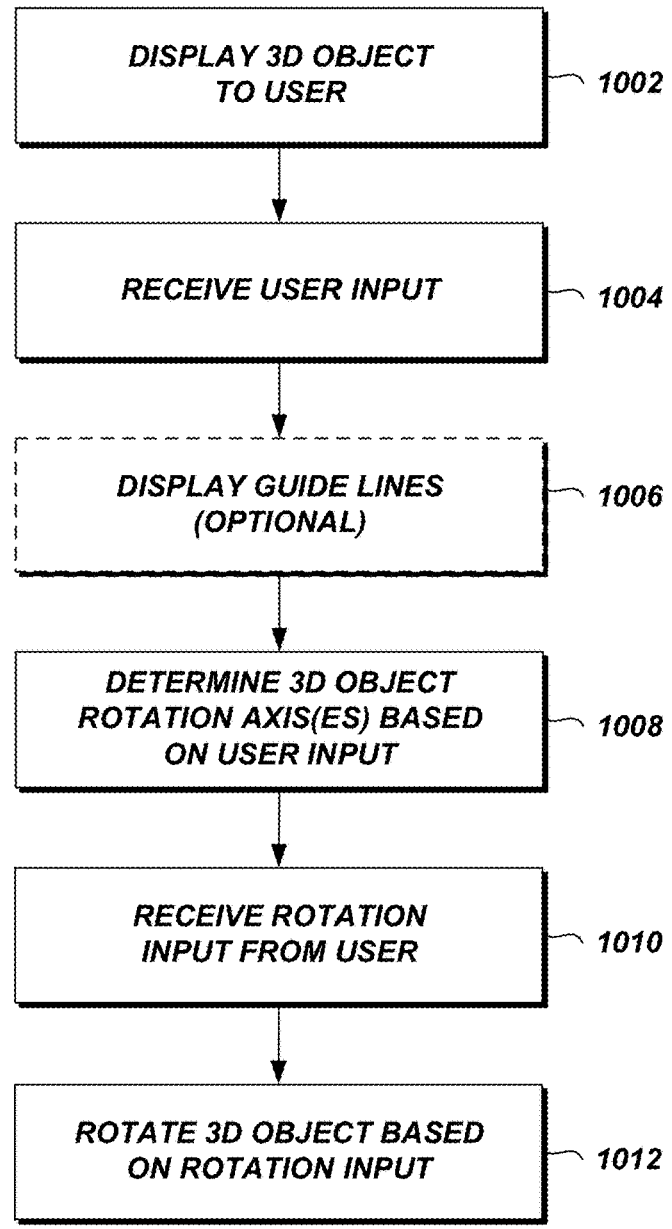
FIG. 10 is a flow diagram depicting an illustrative operation of the system, according to an embodiment of the present disclosure.

FIG. 10 is a flowchart depicting an illustrative operation of the system, according to an embodiment of the present disclosure. The method of FIG. 10 may be stored as a process accessible by, or integrated into, one or more modules as described below in reference to FIG. 1. In various embodiments, the blocks described below may be removed, others may be added, and/or the sequence of the blocks may be altered.

At block 1002, a 3D object is displayed to the user. The 3D object may be displayed on, for example, a touch screen display or any other type of display as described above. At block 1004, an input is received from the user that indicates the type of rotation initiated by the user. For example, in an embodiment, the user may touch a portion of the display indicating that the user wishes to limit rotations to horizontal rotations, or the user may touch another portion of the display indicating that the user wishes to limit rotations to vertical rotations, as described in reference to FIGS. 5B-5E above. Alternatively, the user may provide input via a mouse, and may indicate a rotation axis as described in reference to FIGS. 2-4 above.

At block 1006, guide lines related to the axis or axes of rotation, or other type of movement and/or manipulation, may optionally be display to the user. Display of the guide lines may be accomplished as generally described above. For example, in an embodiment a guide line may be displayed allowing the user to select a particular axis of rotation by, for example, touching, clicking on, and/or rolling over the guide line.

At block 1008, the axis or axes of rotation are determined based on the user input. For example, rotation about a y axis may be determined based on a user touching the bottom or top of the display. In another example, rotation about a z axis may be determined based on the user clicking on, or rolling over, an arced icon with a mouse pointer. Various other axes of rotation may be determined as described above.

At block 1010, rotation input is received from the user. For example, the user may slide a finger across a section of the display, and/or move a mouse pointer along a guide line. At block 1012, the 3D object is rotated based on the received rotation input. For example, the 3D object may be rotated about a horizontal or x axis as the user slides a finger vertically up or down the display. Alternatively, the movement of a mouse pointer may be received, causing rotation of the 3D object. Rotation of the 3D object may be limited or restricted based on the determined axis or axes of rotation of block 1008.

As described above, in an embodiment, guide lines may be displayed that indicate to the user the axis of rotation. In this embodiment, guide lines may be displayed, for example, concurrently with block 1010. In an embodiment, guide lines may be removed from the display once rotation input is received from the user so as to not obscure the 3D object as it is rotated.

In various embodiments, and as described above, other actions may be taken at, for example, block 1012. For example, in an embodiment characteristics of the 3D object may be altered at block 1012 rather than, or in addition to, rotation of the 3D object. Various other embodiments of the present disclosure may likewise be accomplished in corresponding blocks of FIG. 10. In an embodiment, the blocks of FIG. 10 may apply to any multi-dimensional object, such a 2D object.

Example Computing Systems

Figure 1:
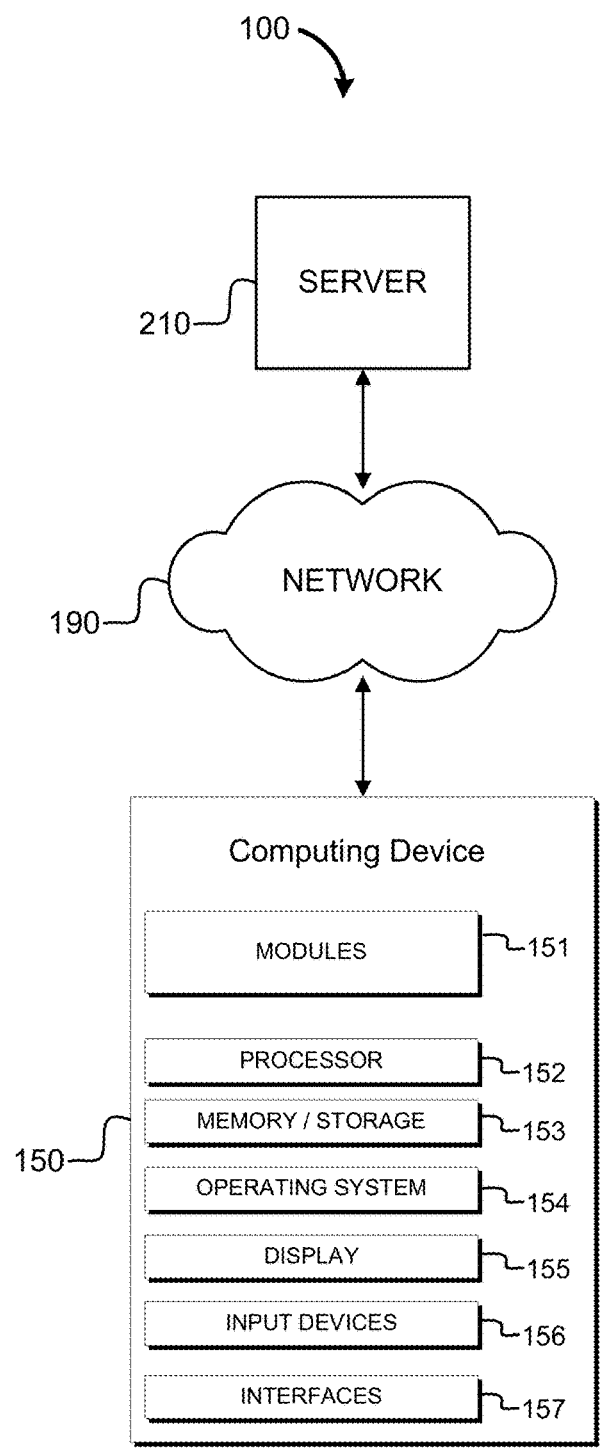
FIG. 1 is a block diagram of a system in which 3D images may be viewed and controlled, according to an embodiment of the present disclosure.

FIG. 1 is a block diagram which shows the various components of a system 100 for displaying information utilizing certain systems and methods described herein. As shown, the system 100 may include an information display computing device 150 (also referred to herein as a "computing device 150") and may include other systems, including those shown in FIG. 1.

The computing device 150 may take various forms. In one embodiment, the information display computing device 150 may be a computer workstation having modules 151, such as software modules that provide the functionality described above with reference to FIGS. 2-10. Examples of such modules may include, for example, a user interface module (that may provide the user interface to the user), a user input module (that may receive touch and/or mouse inputs from the user), and/or an object rotation module (that may determine one or more objects to be rotated, and may further implement rotation of those objects), among other modules. In other embodiments, modules 151 may reside on another computing device, such as the server 210, such that processing that is performed by the modules 151 may be performed by the computing device 150, the server 210, or another computing device, depending on the embodiment. For example, in one embodiment the server 210 includes software modules for rendering and manipulating 3D images (and/or performing any other functions discuss herein), such that the computing device 150 is not required to have similar modules. This "thin client" arrangement may allow a more powerful computing device, for example, the server 210, to perform the computationally intense operations, for example, rotation of 3D images, in order to allow the computing device 150 to view and manipulate 3D images without having to perform such computationally intensive operations.

In an embodiment, the user interface module may be configured to display a multi-dimensional object on an electronic display, such as a display device 155 described below. In an embodiment, the user input module may be configured to receive inputs from a user at particular locations of the electronic display. The inputs may comprise, for example, mouse clicks or touch inputs at particular locations. The input may further indicate, for example, the initiation of a rotation function. In an embodiment, the object rotation module may be configured to access rotation rules associated with the multi-dimensional object. The rotation rules may indicate, for example, planes of rotation available for rotating the multi-dimensional object based on the particular locations of the inputs, as described in the various embodiments of the present description.

In one embodiment, the information display computing device 150 comprises a server, a desktop computer, a workstation, a Picture Archiving and Communication System (PACS) workstation, a laptop computer, a mobile computer, a smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The information display computing device 150 may run an off-the-shelf operating system 154 such as a Windows, Linux, MacOS, Android, or iOS, or mobile versions of such operating systems. The information display computing device 150 may also run a more specialized operating system which may be designed for the specific tasks performed by the computing device 150, or any other available operating system.

The information display computing device 150 may include one or more computing processors 152. The computer processors 152 may include central processing units (CPUs), and may further include dedicated processors such as graphics processor chips, or other specialized processors. The processors generally are used to execute computer instructions based on the information display software modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, JavaScript, ActionScript, Visual Basic, HTML, Lua, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The information display computing device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The information display computing device 150 may also include or be interfaced to one or more display devices 155 that provide information to the users. Display devices 155 may include a video display, such as one or more high-resolution computer monitors, or a display device integrated into or attached to a laptop computer, handheld computer, smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The information display computing device 150 may also include or be interfaced to one or more input devices 156 which receive input from users, such as a keyboard, trackball, mouse, 3D mouse, drawing tablet, joystick, game controller, touch screen (for example, capacitive or resistive touch screen), touchpad, accelerometer, video camera and/or microphone.

The information display computing device 150 may also include one or more interfaces 157 which allow information exchange between information display computing device 150 and other computers and input/output devices using systems such as Ethernet, Wi-Fi, Bluetooth, as well as other wired and wireless data communications techniques.

The modules of the information display computing device 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of information display computing device 150 may be combined into fewer components and modules or further separated into additional components and modules.

The computing device 150 may communicate and/or interface with other systems and/or devices. In one or more embodiments, the computing device 150 may be connected to a computer network 190. The computer network 190 may take various forms. It may include a wired network or a wireless network, or it may be some combination of both. The computer network 190 may be a single computer network, or it may be a combination or collection of different networks and network protocols. For example, the computer network 190 may include one or more local area networks (LAN), wide area networks (WAN), personal area networks (PAN), cellular or data networks, and/or the Internet.

The computing device 150 may be configured to interface with various networked computing devices via the network 190 in order to provide efficient and useful review of data that. The server 210 may include any computing device, such as image acquisition and/or storage devices from which the computing device 150 accesses image data that is usable to generate 3D images for display in the manner discussed above.

Other

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by an Information Display Computing Device and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

Many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, the use of particular terminology when describing certain features or aspects of the invention should not be taken to imply that the terminology is being re-defined herein to be restricted to including any specific characteristics of the features or aspects of the invention with which that terminology is associated.

What is claimed is:

1. A method comprising: by one or more computer processors configured to execute software instructions:
    displaying a multi-dimensional object on a display of a computing system;
    determining boundaries of the multi-dimensional object;
    displaying, on the display, one or more guide lines based on the determined boundaries of the multi-dimensional object, wherein the one or more guide lines indicate one or more available manipulation functions;
    receiving a series of inputs from a user of the computing system, the series of inputs comprising at least a first input followed by a second input, the first input selecting a first location on the display and indicating initiation of a manipulation function of the one or more available manipulation functions and the second input indicating motion from the first location, wherein the manipulation function to be initiated is determined based on a distance between the first location and at least one guide line of the one or more guide lines, the first input comprising at least one of an initial touch input or an initial mouse click at the first location, the second input comprising at least one of a secondary touch input or a movement of a mouse cursor indicating motion from the first location;
    accessing manipulation rules associated with the multi-dimensional object, the manipulation rules indicating at least one of: axes of rotation available for rotating the multi-dimensional object based on the first location, or viewing properties of the multi-dimensional object available for manipulation based on the first location; and
    manipulating, on the display and in proportion to the indicated motion from the first location, the multi-dimensional object, wherein the manipulating is based on: the manipulation rules, the first location, the motion from the first location, and the manipulation function.

2. The method of claim 1, wherein the one or more guide lines do not overlap with the multi-dimensional object.

3. The method of claim 1 further comprising: by the one or more computer processors configured to execute software instructions:
    in response to determining that the first location is to a right side or a left side of the display, and based on the manipulation rules, implementing the manipulation function such that rotation of the multi-dimensional object is limited to rotations about a horizontal axis of the multi-dimensional object, and such that the computing system does not allow rotation of the multi-dimensional object about any other axis until the manipulation function is released;
    in response to determining that the first location is to a top portion or a bottom portion of the display, and based on the manipulation rules, implementing the manipulation function such that rotation of the multi-dimensional object is limited to rotations about a vertical axis of the multi-dimensional object, and such that the computing system does not allow rotation of the multi-dimensional object about any other axis until the manipulation function is released; and
    in response to determining that the first location is near the center of the display, and based on the manipulation rules, implementing the manipulation function such that rotation of the multi-dimensional object is limited to rotations about both the horizontal and vertical axes, and such that the computing system does not allow rotation of the multi-dimensional object about any other axis until the manipulation function is released.

4. The method of claim 3 further comprising: by the one or more computer processors configured to execute software instructions:
    further in response to determining that the first location is to the right side or the left side of the display, displaying one or more horizontal guide lines on the display along at least a portion of the horizontal axis of the multi-dimensional object;
    further in response to determining that the first location is to the top portion or bottom portion of the display, displaying one or more vertical guide lines on the display along at least a portion of the vertical axis of the multi-dimensional object; and
    further in response to determining that the first location is near the center of the display, displaying one or more horizontal guide lines and one or more vertical guide lines on the display along at least a portion of each of the respective horizontal axis of the multi-dimensional object and vertical axis of the multi-dimensional object.

5. The method of claim 1 further comprising: by the one or more computer processors configured to execute software instructions:
    in response to determining that the first location is on or near an icon, and based on the manipulation rules, implementing the manipulation function such that rotation of the multi-dimensional object is limited to at least one of both a horizontal axis and a vertical axis of the multi-dimensional object, or a z-axis of the multi-dimensional object, and such that the computing system does not allow rotation of the multi-dimensional object about any other axis until the manipulation function is released.

6. The method of claim 1 further comprising: by the one or more computer processors configured to execute software instructions:
   adjusting a characteristic of the multi-dimensional object based at least in part on the manipulation function.

7. The method of claim 1 further comprising: by the one or more computer processors configured to execute software instructions:
   in response to determining that the first location is to a right side or a left side of the display, adjusting a first of a plurality of viewing properties of the multi-dimensional object; and
   in response to determining that the first location is to a top portion or a bottom portion of the display, adjusting a second of the plurality of viewing properties of the multi-dimensional object; wherein the viewing properties include at least one of: a brightness, or a contrast.

8. The method of claim 1, wherein characteristics of the one or more guide lines are dynamically adjusted to allow the user to easily recognize the one or more guide lines, and wherein the characteristics comprise at least one of: a position, a spacing, or a thickness.

9. The method of claim 1 further comprising: by the one or more computer processors configured to execute software instructions:
   in response to receiving the series of inputs, removing the guide lines from the display.

10. The method of claim 1, wherein at least one of a vertical axis of the multi-dimensional object, a horizontal axis of the multi-dimensional object, or a z-axis of the multi-dimensional object is defined based on correlation with characteristics of the multi-dimensional object.

11. A computer system comprising: one or more hardware computer processors configured to execute software instructions in order to perform operations comprising:
   displaying a multi-dimensional object on a display of a computing system;
   determining boundaries of the multi-dimensional object;
   displaying, on the display, one or more guide lines based on the determined boundaries of the multi-dimensional object, wherein the one or more guide lines indicate one or more available manipulation functions;
   receiving a series of inputs from a user of the computing system, the series of inputs comprising at least a first input followed by a second input, the first input selecting a first location on the display and indicating initiation of a manipulation function of the one or more available manipulation functions and the second input indicating motion from the first location, wherein the manipulation function to be initiated is determined based on a distance between the first location and at least one guide line of the one or more guide lines, the first input comprising at least one of an initial touch input or an initial mouse click at the first location on the display, the second input comprising at least one of a secondary touch input or followed by a movement of a mouse cursor indicating motion from the first location;
   accessing manipulation rules associated with the multi-dimensional object, the manipulation rules indicating at least one of: axes of rotation available for rotating the multi-dimensional object based on the first location, or viewing properties of the multi-dimensional object available for manipulation based on the first location; and
   manipulating, on the display and in proportion to the indicated motion from the first location, the multi-dimensional object, wherein the manipulating is based on: the manipulation rules, the first location, the motion from the first location, and the manipulation function.

12. The computer system of claim 11, wherein the one or more guide lines do not overlap with the multi-dimensional object.

13. The computer system of claim 11, wherein the one or more hardware computer processors are configured to execute software instructions in order to further perform operations comprising:
   in response to determining that the first location is to a right side or a left side of the display, and based on the manipulation rules, implementing the manipulation function such that rotation of the multi-dimensional object is limited to rotations about a horizontal axis of the multi-dimensional object, and such that the computing system does not allow rotation of the multi-dimensional object about any other axis until the manipulation function is released;
   in response to determining that the first location is to a top portion or a bottom portion of the display, and based on the manipulation rules, implementing the manipulation function such that rotation of the multi-dimensional object is limited to rotations about a vertical axis of the multi-dimensional object, and such that the computing system does not allow rotation of the multi-dimensional object about any other axis until the manipulation function is released; and
   in response to determining that the first location is near the center of the display, and based on the manipulation rules, implementing the manipulation function such that rotation of the multi-dimensional object is limited to rotations about both the horizontal and vertical axes, and such that the computing system does not allow rotation of the multi-dimensional object about any other axis until the manipulation function is released.

14. The computer system of claim 13, wherein the one or more hardware computer processors are configured to execute software instructions in order to further perform operations comprising:
   further in response to determining that the first location is to the right side or the left side of the display, displaying one or more horizontal guide lines on the display along at least a portion of the horizontal axis of the multi-dimensional object;
   further in response to determining that the first location is to the top portion or bottom portion of the display, displaying one or more vertical guide lines on the display along at least a portion of the vertical axis of the multi-dimensional object; and
   further in response to determining that the first location is near the center of the display, displaying one or more horizontal guide lines and one or more vertical guide lines on the display along at least a portion of each of the respective horizontal axis of the multi-dimensional object and vertical axis of the multi-dimensional object.

15. The computer system of claim 11, wherein the one or more hardware computer processors are configured to execute software instructions in order to further perform operations comprising:
   in response to determining that the first location is on or near an icon, and based on the manipulation rules, implementing the manipulation function such that rotation of the multi-dimensional object is limited to at least one of both a horizontal axis and a vertical axis of the multi-dimensional object, or a z-axis of the multi-dimensional object, and such that the computing system does not allow rotation of the multi-dimensional object about any other axis until the manipulation function is released.

16. A non-transitory computer-readable medium storing software instructions configured for execution by a computing system having one or more hardware processors in order to cause the computing system to perform operations comprising:
  displaying a multi-dimensional object on a display of the computing system; determining boundaries of the multi-dimensional object;
  displaying, on the display, one or more guide lines based on the determined boundaries of the multi-dimensional object, wherein the one or more guide lines indicate one or more available manipulation functions;
  receiving a series of inputs from a user of the computing system, the series of inputs comprising at least a first input followed by a second input, the first input selecting a first location on the display and indicating initiation of a manipulation function of the one or more available manipulation functions and the second input indicating motion from the first location, wherein the manipulation function to be initiated is determined based on a distance between the first location and at least one guide line of the one or more guide lines, the first input comprising at least one of an initial touch input or an initial mouse click at the first location, the second input comprising at least one of a secondary touch input or a movement of a mouse cursor indicating motion from the first location;
  accessing manipulation rules associated with the multi-dimensional object, the manipulation rules indicating at least one of: axes of rotation available for rotating the multi-dimensional object based on the first location, or viewing properties of the multi-dimensional object available for manipulation based on the first location; and
  manipulating, on the display and in proportion to the indicated motion from the first location, the multi-dimensional object, wherein the manipulating is based on: the manipulation rules, the first location, the motion from the first location, and the manipulation function.

17. The non-transitory computer-readable medium of claim 16, wherein the software instructions are configured for execution by the computing system in order to cause the computing system to further perform operations comprising:
  in response to determining that the first location is to a right side or a left side of the display, adjusting a first of a plurality of viewing properties of the multi-dimensional object; and
  in response to determining that the first location is to a top portion or a bottom portion of the display, adjusting a second of the plurality of viewing properties of the multi-dimensional object; wherein the viewing properties include at least one of: a brightness, or a contrast.

18. The non-transitory computer-readable medium of claim 16, wherein characteristics of the one or more guide lines are dynamically adjusted to allow the user to easily recognize the one or more guide lines, and wherein the characteristics comprise at least one of: a position, a spacing, or a thickness.

19. The non-transitory computer-readable medium of claim 16, wherein the software instructions are configured for execution by the computing system in order to cause the computing system to further perform operations comprising:
  in response to receiving the series of inputs, removing the guide lines from the display.

20. The non-transitory computer-readable medium of claim 16, wherein at least one of a vertical axis of the multi-dimensional object, a horizontal axis of the multi-dimensional object, or a z-axis of the multi-dimensional object is defined based on correlation with characteristics of the multi-dimensional object.

* * * * *